United States Patent
Beppu

(10) Patent No.: US 6,676,410 B2
(45) Date of Patent: Jan. 13, 2004

(54) GRINDING BAR

(75) Inventor: Hisashi Beppu, Tokyo (JP)

(73) Assignee: Hinatawada Seimitsu Mfg., Ltd., Tokyo (JP)

( * ) Notice: Subject to any disclaimer, the term of this patent is extended or adjusted under 35 U.S.C. 154(b) by 0 days.

(21) Appl. No.: 10/282,466

(22) Filed: Oct. 29, 2002

(65) Prior Publication Data

US 2003/0232307 A1 Dec. 18, 2003

(30) Foreign Application Priority Data

Jun. 14, 2002 (JP) ........................ 2002-173969

(51) Int. Cl.$^7$ .................................................. A61C 3/06
(52) U.S. Cl. ...................................................... 433/166
(58) Field of Search ................................ 433/165, 166, 433/142, 102

(56) References Cited

U.S. PATENT DOCUMENTS

| | | | | |
|---|---|---|---|---|
| 636,359 A | * | 11/1899 | Schultz | |
| 685,659 A | * | 10/1901 | Williams | |
| 4,661,061 A | * | 4/1987 | Martin | 433/102 |
| 5,066,230 A | * | 11/1991 | Weissman | 433/165 |
| 5,735,690 A | * | 4/1998 | Malentacca | 433/102 |
| 5,779,476 A | * | 7/1998 | Roetzer et al. | 433/165 |

* cited by examiner

Primary Examiner—Cary E. O'Connor
(74) Attorney, Agent, or Firm—McGlew and Tuttle, P.C.

(57) ABSTRACT

A grinding bar capable of stably staying a grinding part in a minute part of an affected part to execute a grinding and treatment in an environment having a large visual field is provided. This grinding bar to be mounted on a hand piece and used for grinding a tooth comprises a shank part 12 to be mounted on the hand piece, a tapered neck part 13 provided continuously to the shank part 12, a rod part B provided continuously to the neck part 13 and narrower and longer than the neck part 13, and an arrowhead-like or piece-like grinding part 15 formed by fixing diamond particles to the tip of the rod part B.

15 Claims, 5 Drawing Sheets

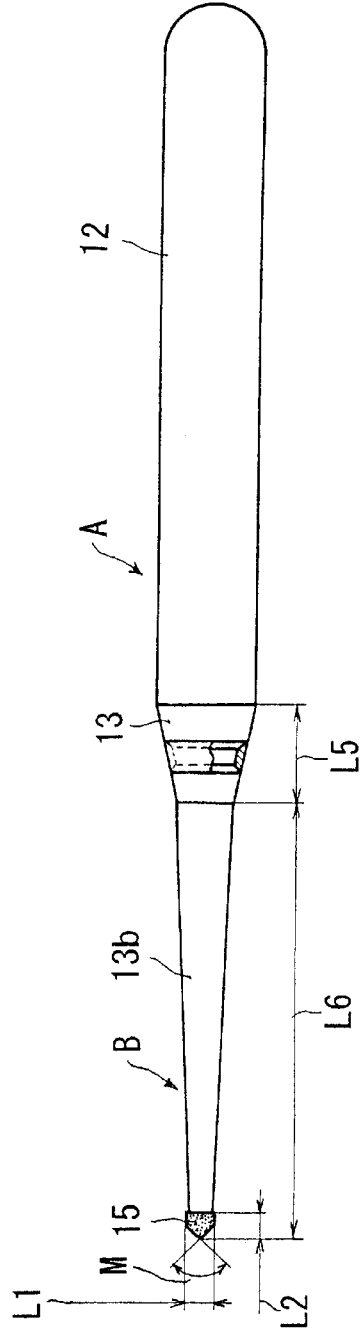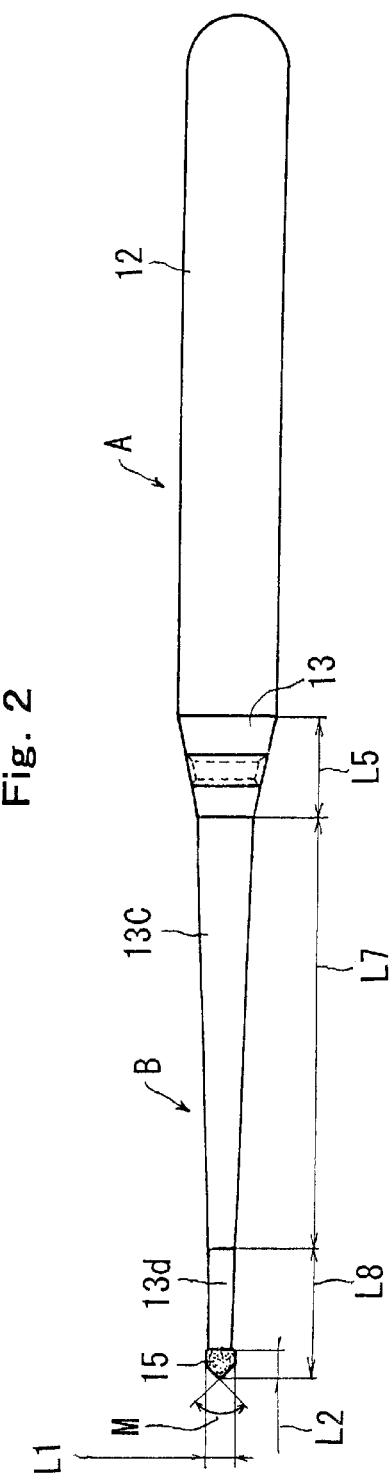

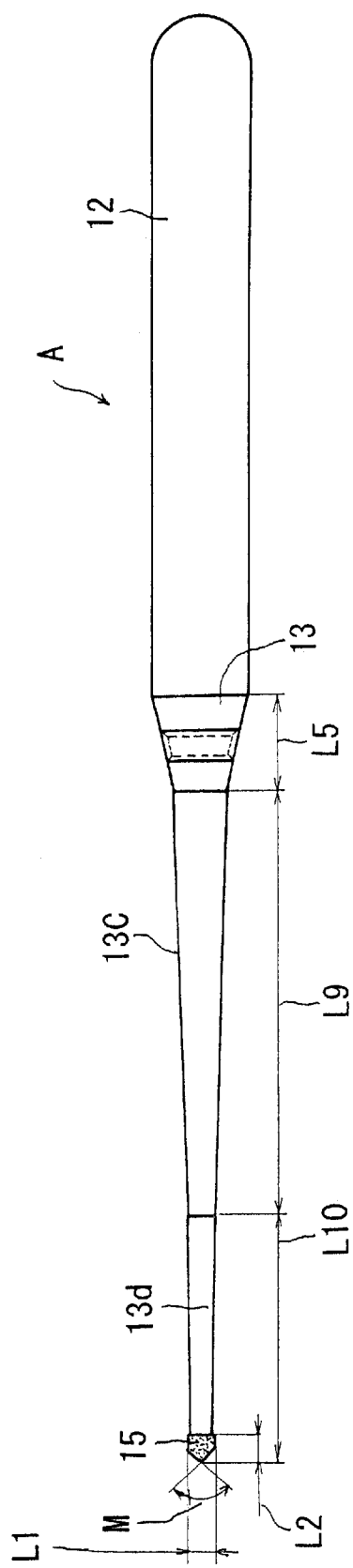

Fig. 7
(A)
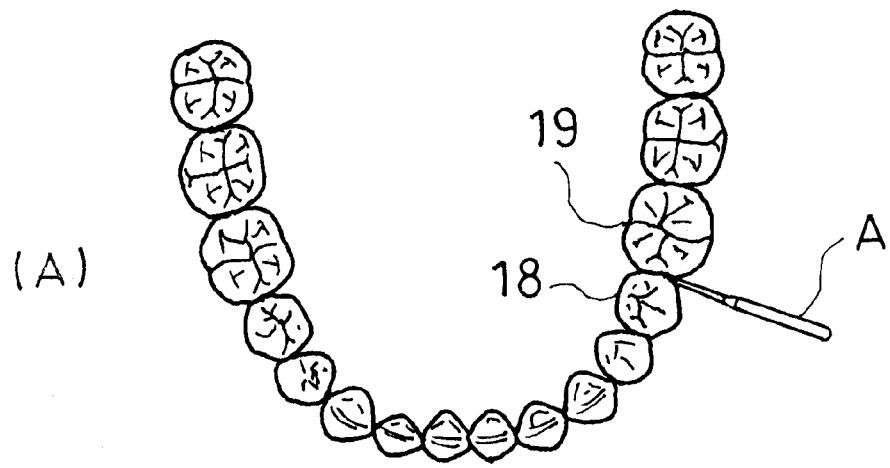
(B)
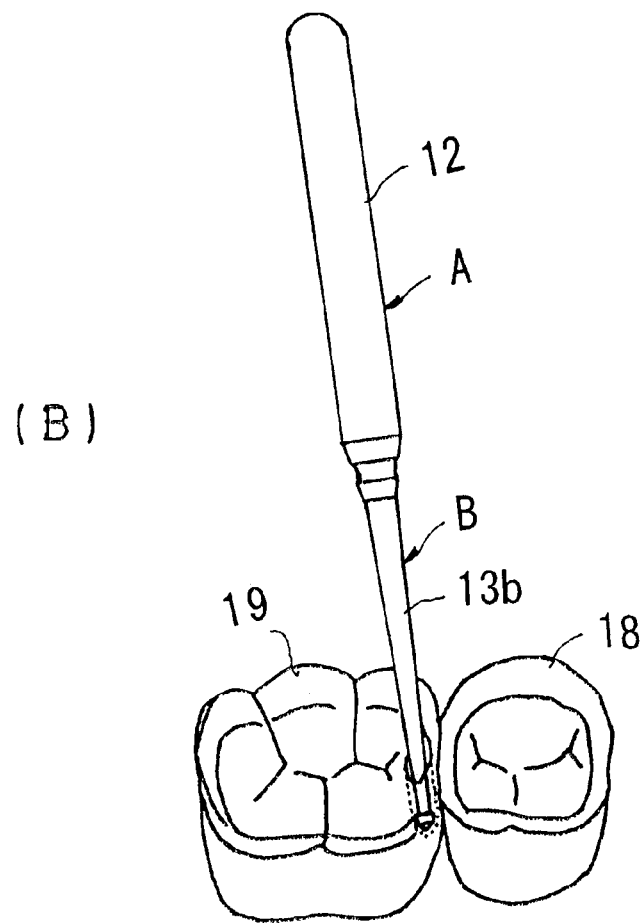

Fig. 8    (PRIOR ART)
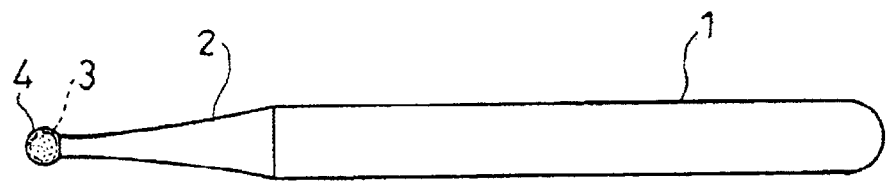
Fig. 9    (PRIOR ART)
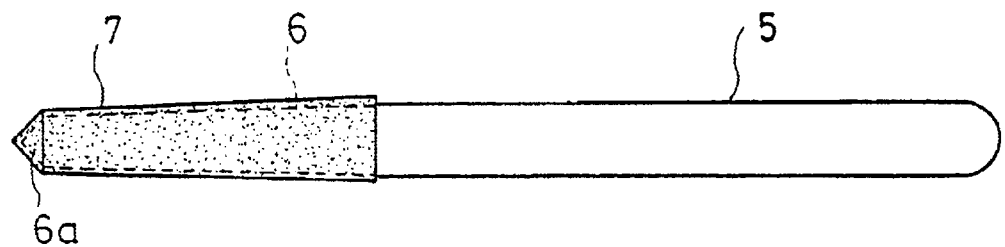
Fig. 10    (PRIOR ART)
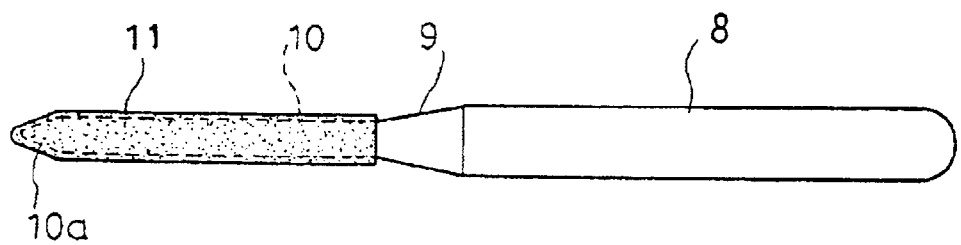

GRINDING BAR

BACKGROUND OF THE INVENTION

This invention relates to a grinding bar to be mounted on a dental hand piece and used for grinding or treating a tooth.

In odontotherapy, a dental hard tissue broken by Streptococcus mutans or the like is ground by the use of a diamond bar.

As such a diamond bar, various types are available according to the purpose, and those shown in FIGS. 8, 9 and 10, for example, are known.

FIG. 8 shows a conventional small-sized round type diamond bar. This diamond bar comprises a shank part 1 to be mounted on a hand piece, a neck part 2 continued to the shank part 1 and reduced in diameter toward the tip in a tapered shape, a tip spherical part 3 continued to the neck part 2, and a grinding part 4 formed by fixing diamond particles to the whole circumference of the spherical part 3.

FIG. 9 shows another conventional diamond bar, which comprises a shank part 5, a tapered part 6 continued to the shank part 5 and having a conical part 6a at the tip, and a grinding part 7 formed by fixing diamond particles to the circumferential surface of the tapered part 6.

FIG. 10 similarly shows a further conventional diamond bar, which comprises a shank part 8, a short tapered neck part 9 provided continuously to the shank part 8, a round bar-like shaft part 10 connected to the neck part 9 and smaller in diameter than the shank part 8, and a grinding part 11 formed by fixing diamond particles to the circumferential surface of the shaft part 10.

The diamond bars as conventional grinding bars have the following disadvantages.

In the bar shown in FIG. 8, the comprehensive orientation of preciseness, safely, centripetal property and the like is insufficient. Namely, the contact surface to tooth of the grinding part 4 is unstable because of the spherical shape, so that an extremely narrow treatment part such as a fine fissure in a crown part or the like cannot be precisely caught. Particularly, the grinding part 4 often slips and moves on a hard tooth surface in grinding to grind an extra part other than the part requiring the treatment.

This problem cannot be solved only by simply minimizing the spherical diameter.

In the positioning of the grinding part 4 to a treatment portion, an extra force is applied to the fingers holding a hand piece in order to prevent the slippage or movement caused by the spherical shape of the diamond bar, and this gives a psychologically large stress to dentists.

In the diamond bar having the spherical grinding part 4 as shown in FIG. 8, it is difficult to feel the difference between a carious part and a non-carious part by the fingers in the grinding of a tooth because the dental hand piece must be operated with a strong force applied to the fingertips as described above, causing the problem of the difficulty in precisely judging the grinding quantity.

In a sound dental hard tissue, the enamel Knoop hardness is 5.5, but the hardness is successively reduced according to the progress of caries.

Thus, if the grinding part can precisely catch and grind a treatment position without movement, dentists can be released from the psychological stress and clearly feel the difference in hardness through their fingerprints.

In the diamond bars shown in FIGS. 9 and 10, the grinding parts 7 and 11 cannot precisely catch a small treatment part because of their large outer diameters and axial lengths, and this introduces the danger of grinding an extra part.

Particularly, the visual field from the outside of the oral cavity to the inside is obstructed to make the treatment of a tooth difficult, resulting in the grinding of the tooth in an unnecessary wide area.

These bars are basically used for partially or entirely replacing the tooth crown with metal or ceramics, and it is regarded that the grinding of a sound crown cannot be avoided for the purpose.

In the treatment of a partial carious part between adjacent teeth, the grinding parts 7 and 11 hardly reach the limited carious part between the teeth because of the large tip diameters thereof, and the difficulty of orientation increases the danger of excessively grinding the teeth.

Accordingly, although a dental physic based on the idea that the invasion to a dental hard tissue should be minimized has been proposed in the international dental field, the conventional bars cannot satisfy this proposal.

SUMMARY OF THE INVENTION

The present invention thus has an object to provide a grinding bar capable of removing only an affected part of a minute range with a minimum grinding by allowing a grinding part, when put on the treatment part of a tooth, to stably stay in a point of a designated treatment part and perform a continuous grinding, and further surely and easily grinding and treating only a carious part by sufficiently ensuring the visual field from the outside of the oral cavity to the inside so as to easily catch the difference in hardness of dentine.

To attain the above purpose, the present invention provides a grinding bar to be mounted on a hand piece and used for grinding a tooth, comprising a shank part to be mounted on the hand piece, a tapered neck part provided continuously to the shank part, a rod part provided continuously to the neck part and more slender than the neck part, and an arrowhead-like or separate piece-like grinding part formed by fixing diamond particles to the tip of the rod part.

The grinding part is formed in outer diameters ranging from 0.4 to 0.6 mm, lengths ranging from 0.4 to 0.6 mm, and tip conical angles ranging from 60 to 120°. The grinding part 15 is preferably formed so as to have an outer diameter of 0.47 mm, a length of 0.47 mm, and a tip conical angle of 90°.

The rod part is preferably formed of a single tapered shaft having a taper converged to the tip.

The rod part may be formed of a shaft having a taper converged to the tip and a straight shaft continued to the shaft.

The rod part may be formed of a single straight and slender shaft.

BRIEF DESCRIPTION OF THE DRAWINGS

FIG. 1 is a front view showing a first embodiment of a grinding bar according to the present invention.

FIG. 2 is a front view showing another embodiment of a grinding bar according to the present invention.

FIG. 3 is a front view showing a further embodiment of a grinding bar according to the present invention.

FIG. 4 is an enlarged front view of a grinding part.

FIGS. 7 (A) and (B) are views showing the grinding state of a tooth by a grinding bar according to the present invention.

FIG. 8 is a front view of a conventional grinding bar.

FIG. 9 is a front view of another conventional grinding bar.

FIG. 10 is a front view of a further conventional grinding bar.

DETAILED DESCRIPTION OF THE PREFERRED EMBODIMENT

Figure 5:
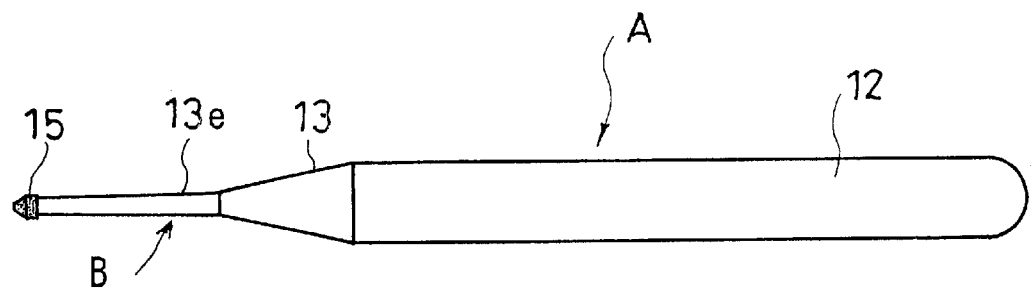
FIG. 5 is a front view showing an even further embodiment of a grinding bar according to the present invention.

Preferred embodiments of the present invention will be further described in reference to the drawings.

In a diamond bar that is a grinding bar A according to the embodiments of the present invention, as shown in FIGS. 1, 2, 3 and 5, the grinding part 15 is not only minimized in order to further ensure the orientation so that only a target part can be more safely removed in an extended visual field, but alto molded into an arrowhead-like or piece-like outer shape, when seen from the front, in order to prevent the slippage on a tooth surface to minimize the movement in biting as much as possible. Further, a rod part is formed into a slender and smooth tapered shape so that the visual field can be extended to surely transmit the change in hardness of dentine received by the tip grinding part to the hand in grinding.

Namely, the basic form of the grinding bar shown in each of FIGS. 1, 2, 3 and 5 is formed of a shank part 12 to be mounted on a hand piece, a tapered neck part 13 provided continuously to the shank part 12, the rod part B provided continuously to the neck part 13 and more slender than the neck part 13, and the arrowhead-like or piece-like grinding part 15 formed by fixing diamond particles to the tip of the rod part B.

Any grinding bar is usable as long as the neck part 13 is formed in lengths L5 ranging from 1 to 6 mm, and the grinding part 15 is formed in outer diameters L1 ranging from 0.4 to 0.6 mm, lengths L2 ranging from 0.4 to 0.6 mm, and tip conical angles M ranging from 60 to 120°. Actually, however, it has been apparent from experimental results that the grinding bar is preferably formed so that the neck part 13 has a length L5 of 1.6 mm, and the grinding part 15 has an outer diameter L1 of 0.47 mm, a length L2 of 0.47 mm, and a tip conical angle M of 90°.

In the grinding bar A of FIG. 1, the rod part B is formed of a single tapered shaft 13b having a taper converged toward the tip.

In the grinding bars A of FIGS. 2 and 3, the respective rod part B is formed of a shaft 13c having a taper converged toward the tip and a straight shaft 13d continued to the shaft 13c.

In this case, the both have the same structure, but the shaft 13d of FIG. 3 is formed longer than that of FIG. 2 as described later.

It is clinically proved that the change in hardness of dentine can be more clearly transmitted to the hand as the shaft 13d is longer.

The grinding bar A of FIG. 5 has substantially the same structure as the grinding bar A of FIG. 1, but the rod part B is formed of a single straight and slender shaft 13e.

In the grinding bars A shown in FIGS. 2 and 3, the rod part B is extended so as to be suitably used to remove an infected dentin on the reverse side of enamel or in the state where it reaches a narrow and deep cavity.

The whole length of each grinding bar A can be optionally selected according to the purpose.

Namely, the grinding bar A is molded in lengths ranging from 17 to 25 mm because the inserting depth of the dental hand piece to be selected is varied according to the purpose of use.

The length, thickness and outer shape of the neck part 13 and the rod part B are also selected every time according to the purpose of use.

Figure 6:
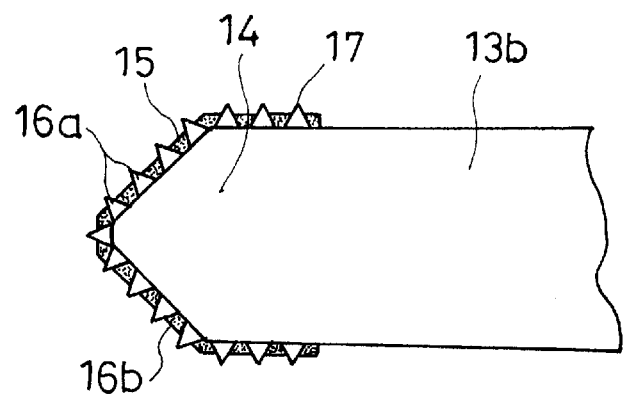
FIG. 6 is an enlarged sectional view of a grinding bar according to the present invention.

As the particles, diamond particles 16a with a particle size of 40–50 μm are used, for example, as shown in FIGS. 4 and 6, and these are laid in the form fixed by an electroplating layer 16b of nickel or the like.

As shown in FIG. 4, the length L2 of the grinding part 15 is the total of the height L3 of a conical part (a) and the length L4 of a cylindrical part (b), and the cylindrical part (b) is formed in a straight or tapered shape within the range of 0–3°.

The rod part B of the grinding bar A shown in FIG. 1 has a length L6 of 7 mm.

The shaft 13c of the grinding bar A shown in FIG. 2 is formed so that the length L7 is 7 mm, and the length L8 on the tip side from the shaft 13d is 2 mm.

The grinding bar of FIG. 5 has the long neck part 13 and the short rod part B, compared with that of FIG. 1.

When an affected part is treated by use of the grinding bar A according to the present invention as described above, the shank part 12 is first chucked to a dental hand piece.

The grinding bar A is driven at an ultrahigh speed, and the grinding part 15 is lightly touched to a tooth carious part in the oral cavity.

For example, the grinding part 15 of the grinding bar A is brought into contact so that the tip is placed on a part of a fissure in a crown.

The grinding part 15 stays in one point of the part to be treated without moving because of its small arrowhead-like or separate piece-like shape, and grinds only this part.

A part other than the intended part is never ground in an extended visual filed. At this time, the difference between the affected part and the non-affected part can be felt by the fingertips. A part other than the intended part is never ground in an extended visual filed. At this time, the difference between the affected part and the non-affected part can be felt by the fingertips.

When the grinding is continued, the conical surface at the tip of the grinding part 15 is advanced into the crown according to the case to extend the grinding area, and a necessary quantity of grinding treatment can be thus performed.

When the affected part is large, the small conical surface or small width circumferential surface of the grinding part 15 grinds the affected part by moving the dental hand piece to a necessary position, and a necessary minimum quantity of grinding can be performed.

The grinding part 15 does not slip on the tooth surface because of satisfactory orientation, and can grind the affected part only by being lightly touched thereto. Therefore, dentists can clearly feel the tip without applying an extra force to the hand or fingers holding the hand piece.

Thus, the dentists can perform a treatment in relaxed conditions.

When it is desired to perform the grinding of a carious part within a visual field magnified by a microscope or loupe in order to grind only the affected part, the grinding part 15 can be precisely and easily moved to the point of the affected part because of its small size, and a sound tissue or restorable tissue can be protected.

In this case, since the rod part B of the grinding bar A is formed slender, the visual field can be sufficiently ensured to facilitate a precise treatment work.

Particularly, since the rod part 13b is gently tapered toward the tip, the movement of the grinding part 15 to the point is also visually facilitated.

Further, the touch of the tip can be easily transmitted to the hand, and a double effect can be obtained.

The straight shaft 13d continued to the shaft 13c of FIG. 2 is added, whereby the reachability is enhanced, so that the dentin part of the caries extending in the boundary between enamel and dentin of a tooth can be laterally ground by the grinding part 15 while leaving the enamel on the surface as much as possible.

Further, since a chin (stepped part) 17 is formed in the short grinding part 15 provided at the end of the slender rod part 13 as shown in FIG. 6, a laterally extending caries can be easily ground without largely extending the sound enamel by use of the chin part 17.

Further, the grinding part 15 can safely and efficiently remove a carious part formed in adjacent parts of teeth 18 and 19 without making contact with the other part, as shown in FIG. 7(A) because it is formed as thin as 0.47 mm.

In this case, also, the laterally extending caries can be removed without largely grinding the sound enamel.

In a tunneling operation for removing the caries of adjacent parts from the occlusal surface without breaking the adjacent surfaces of sound teeth 18 and 19, as shown in FIG. 7(B), the grinding part 15 is most suitable since it has the small size and satisfactory orientation so that the difference in hardness can be felt.

According to the embodiments of the present invention, the following effects can be obtained.

The orientation can be further ensured to more safely remove only a target part in an extended visual field.

Particularly, since the grinding part 15 is formed in a small arrowhead-like or separate piece-like shape with outer diameters ranging from 0.4 to 0.6 mm, lengths ranging from 0.4 to 0.6 mm, and tip conical angles ranging from 60 to 120°, the careless slippage on the tooth surface can be prevented to minimize the movement in biting as much as possible.

Since the arrowhead-like grinding bar catches, different from a conventional round type one, the dentin not by a spherical surface but the conical surface near the apex of the arrowhead, the orientation can be extremely enhanced, and the centripetal property can be also remarkably Therefore, the grinding part 15 is not made to slip even on the glossy and slippery enamel surface, and the orientation and centripetal property of the grinding part 15 can be ensured. Thus, only a target part can be ground almost without grinding an extra tissue, compared with a conventional product.

Further, since the slender rod part is adapted, not only a minimized grinding can be performed, but also the infected dentin on the inside of the enamel can be precisely removed without being obstructed by the enamel according to the characteristic of the caries rapidly extending to the dentin side in the enamel-dentin boundary, and the sound enamel can be thus reserved as much as possible.

The sharp tip of the grinding part can be precisely stayed with good orientation to a tooth to precisely and lightly grind a minute affected part without movement, and an extra force can be prevented from being applied to the hand grasping the dental hand piece to reduce the dentists' psychological loads in working.

Further, this grinding bar can be inserted into any minute clearance of teeth to perform a sufficient grinding, the positioning of the grinding part to a treatment necessary part can be visually facilitated, and the difference in hardness in the tip part can be clearly transmitted to the hand holding the hand piece. Accordingly, the effect that the grinding of an unnecessary part can be avoided can be obtained.

What is claimed is:

1. A grinding bar to be mounted on a hand piece and used for grinding a tooth, the grinding bar comprising a shank part to be mounted on the hand piece, a tapered neck part provided extending continuously to the shank part, a rod part provided extending continuously to the neck part, the rod part being longer and more slender than the neck part, a conical part on a tip of the rod part and a grinding part formed of diamond particles affixed to the tip of the rod part, wherein the grinding part includes the conical part and a cylindrical part and a length of the cylindrical part and the conical part together is approximately equal to a diameter of the rod part.

2. A grinding bar according to claim 1 wherein the grinding part is formed in outer diameters ranging from 0.4 to 0.6 mm, lengths ranging from 0.4 to 0.6 mm, and tip conical angles ranging from 60 to 120°.

3. A grinding bar according to claim 1 wherein the grinding part is formed in an outer diameter of 0.47 mm, a length of 0.47 mm, and a tip conical angle of 90°.

4. A grinding bar according to claim 1 wherein the rod part is formed of a single tapered shaft having a taper converged toward the tip.

5. A grinding bar according to claim 1 wherein the rod part is formed of a shaft having a taper converged to the tip and a straight shaft continued to the shaft.

6. A grinding bar according to claim 1 wherein the rod part is formed of a single straight and slender shaft.

7. A grinding bar according to claim 1 wherein said grinding part includes the conical part and the cylindrical part formed into an angular shape at a joint point between the conical part and the cylindrical part.

8. A grinding bar to be mounted on a hand piece and used for grinding a tooth, the grinding bar comprising:
 a shank portion to be mounted on the hand piece;
 a tapered neck portion extending continuously from said shank portion;
 a rod portion extending continuously from said neck portion to a rod tip, said rod portion being longer than said neck position and said rod position having an end diameter adjacent to said rod tip that is smaller than a diameter of said neck portion;
 a grinding portion at said rod tip, said grinding portion including a conical tip portion and a cylindrical portion and including diamond particles affixed to said conical tip portion and said cylindrical portion, said grinding portion having a length approximately equal to said end diameter of said rod portion.

9. A grinding bar according to claim 8, wherein the grinding portion has an outer diameter ranging from 0.4 to 0.6 mm, a length ranging from 0.4 to 0.6 mm, and a tip conical angle ranging from 60 to 120°.

10. A grinding bar according to claim 8, wherein the grinding portion has an outer diameter of 0.47 mm, a length of 0.47 mm, and a tip conical angle of 90°.

11. A grinding bar according to claim 8, wherein the rod portion has a single tapered shaft having a taper converged toward the tip.

12. A grinding bar according to claim 8, wherein the rod portion has a shaft portion having a taper converging to said rod tip and has a straight shaft portion connected to said shaft portion.

13. A grinding bar according to claim 8, wherein the rod portion is formed of a single straight shaft.

14. A grinding bar according to claim 8, wherein said grinding portion includes said conical portion and said cylindrical portion formed into an angular shape at a joint point between said conical portion and said cylindrical portion.

15. A grinding bar to be mounted on a hand piece and used for grinding a tooth, the grinding bar comprising:

a shank portion to be mounted on the hand piece;

a tapered neck portion extending continuously from said shank portion;

a rod portion extending continuously from said neck portion to a rod tip, said rod portion being longer than said neck portion and said rod portion having a straight portion with an end diameter adjacent to said rod tip that is smaller than a diameter of said neck portion;

a grinding portion at said rod tip, said grinding portion including a conical tip portion and a cylindrical portion and including diamond particles affixed to said conical tip portion and said cylindrical portion such that said grinding portion has a diameter larger than said end diameter of said rod portion, said grinding portion having a length approximately equal to said end diameter of said rod portion and having a joint point forming an angle at a transition between said conical portion and said cylindrical portion.

\* \* \* \* \*